United States Patent [19]
Guigui et al.

[11] Patent Number: 5,674,186
[45] Date of Patent: Oct. 7, 1997

[54] HALO CONSISTING OF POSITIONALLY ADJUSTABLE ELEMENTS AND CAPABLE OF BEING FIXED IN A PLURALITY OF ADJUSTABLE POSITIONS ON THE CRANIUM OF A PATIENT

[75] Inventors: Pierre Guigui; Kervan Mazda, both of Paris, France; Olivier Pierron, Luxembourg, Luxembourg

[73] Assignee: Etablissements Proteor, Dijon, France

[21] Appl. No.: 612,563

[22] Filed: Mar. 8, 1996

[30] Foreign Application Priority Data

Sep. 3, 1995 [FR] France ................... 95 02758

[51] Int. Cl.⁶ .................................................. A61F 5/00
[52] U.S. Cl. ........................ 602/17; 606/54; 606/56
[58] Field of Search ............... 602/17–19; 606/53, 606/54, 56, 58, 59

[56] References Cited

U.S. PATENT DOCUMENTS

| | | | |
|---|---|---|---|
| 678,417 | 7/1901 | Muller | 602/17 |
| 3,072,118 | 1/1963 | Standerwick et al. | 602/17 |
| 3,391,693 | 7/1968 | Georgiade et al. | 602/17 |
| 4,541,421 | 9/1985 | Iversen et al. | 602/18 |
| 5,062,415 | 11/1991 | Weatherby et al. | 602/18 X |
| 5,156,588 | 10/1992 | Marcune et al. | |
| 5,195,947 | 3/1993 | Bode | 602/17 X |
| 5,203,765 | 4/1993 | Friddle, Jr. | 602/18 |
| 5,302,170 | 4/1994 | Tweardy | 602/17 |

FOREIGN PATENT DOCUMENTS

WO 88/04541  6/1988  WIPO.

*Primary Examiner*—Linda C. Dvorak
*Attorney, Agent, or Firm*—Scully, Scott, Murphy & Presser

[57] ABSTRACT

A halo adapted to enclose the forehead and temples of a patient including at least two frontotemporal bars (1) which are joined to each other, and two half-arches (2) which are joined to each other and are fixed connected with the frontotemporal bars, the joined half-arches forming an arch enclosing the posterosuperior zone of the cranium of the patient. The frontotemporal bars (1) and the half-arches (2) are interconnected through bars (4, 5) overlapping the contiguous ends of the former. The mutually facing portions of the frontotemporal bars, the half-arches and the interconnecting bars include orifices (7, 8, 9, 10, 11, 12) facilitating rigid fastening together thereof by assembly screws (6). At least some of the orifices of the interconnecting bars, the frontotemporal bars, and the half-arches being oblong slots (7, 8, 12), facilitating adapting the dimensions of the halo to the morphology of the cranium of the patient.

10 Claims, 4 Drawing Sheets

HALO CONSISTING OF POSITIONALLY ADJUSTABLE ELEMENTS AND CAPABLE OF BEING FIXED IN A PLURALITY OF ADJUSTABLE POSITIONS ON THE CRANIUM OF A PATIENT

BACKGROUND OF THE INVENTION

1. Field of the Invention

The present invention rerates to a halo consisting of positionally adjustable elements and capable of being fitted in a plurality of adjustable positions on the cranium of a patient.

2. Discussion of the Prior Art

It is known that, in the treatment of various conditions of the spinal column due to injuries or deformations, it is necessary to exert traction on the spinal column in the region of the cervical vertebrae. To this end, a rigid structure which often has a circular profile, from which it has acquired the name "halo", is fixed on the braincase of the patient with the aid of setting screws or the like, and this halo is made rigidly integral, in a defined position, with a frame which is integral with the thoracic cage of the patient, by way of a corset for example.

SUMMARY OF THE INVENTION

The invention aims to propose a halo which is both adjustable in dimensions and adjustable in position on the cranium of the patient, in such a way that it can be adapted to braincases with different morphologies and dimensions, and thereby to reduce the number of halos kept ready for use.

To this end, the subject of the invention is a halo of the type including at least two frontotemporal bars which are joined to each other and are intended to enclose the forehead and the temples of the patient, and two half-arches which are joined to each other and are made integral with the frontotemporal bars, the joined half-arches being intended to form an arch enclosing the posterosuperior zone of the cranium of the patient, this halo being characterized in that the frontotemporal bars and/or the half-arches are joined together with the aid of small bars overlapping their contiguous ends, the mutually facing parts of the frontotemporal bars, the half-arches and the small bars comprising orifices allowing them to be made integral with the aid of assembly means, such as screws, at least some of the orifices of the small bars and/or the frontotemporal bars and/or the half-arches being in the form of oblong slots, making it possible to adjust the overlap of the small bars and the ends of the associated components and thereby to adapt the dimensions of the halo to the morphology of the cranium of the patient.

The frontotemporal bars and the half-arches will be able to be joined directly to each other and, in this case, these components will include mutually overlapping contiguous end parts in which orifices will be formed, allowing them to be made integral with each other with the aid of assembly means, such as screws, some of the orifices of the associated end parts of the frontotemporal bars and/or the half-arches being in the form of oblong slots, making it possible to adjust their overlap and thereby to adapt the dimensions of the halo.

It will also be possible for the half-arches to be connected to the frontotemporal bars via joining components partially overlapping the contiguous ends of the frontotemporal bars, and, in this case, orifices will be formed in the mutually facing parts of these joining components and of the frontotemporal bars, with a view to making them rigidly integral with the aid of assembly means such as screws, some of the orifices of the joining components and/or of the frontotemporal bars being in the form of oblong slots, so as to be able to join them together in a plurality of positions.

In this embodiment, the half-arches and the joining components will advantageously be connected by small bars overlapping their contiguous ends, orifices being formed for assembly means, such as screws, in the facing parts of the half-arches and the joining components, some of the orifices of these bars and/or of these components being in the form of oblong slots, so as to be able to join them together in a plurality of positions.

The halo will also comprise occipital bars which are intended to bear opposite the occiput of the patient. These occipital bars will be integral with the ends of the half-arches or the joining components contiguous with the frontotemporal bars, and, so as to be able to join them together in a plurality of positions with the aid of assembly means such as screws, in order to be able to select the position best adapted to the morphology of the cranium of the patient, mutually facing orifices will be provided in the ends of the half-arches, the joining components and/or the occipital bars, and at least some of these orifices will be in the form of oblong slots.

The invention thus affords a simple means, which is easy to use, for adapting the dimensions of the halo to those of the cranium of the patient who is to be fitted with this halo, and to the morphology thereof.

The setting screws or similar which are used to fix the halo on the braincase of the patient will preferably be engaged in oblong slots in the frontotemporal bars and occipital bars, in such a way as to be able to adjust their position, and their diameter will be slightly smaller than the width of the oblong slots, in such a way as to be able to orient them optimally in relation to the cranium of the patient.

As will be seen in greater detail hereinafter, for the purpose of being able in a simple way to confer a flexion or extension movement on the cranium and cervical spine unit, it will be advantageously possible for the end of one half-arch and/or one frontotemporal bar to be mounted pivotably with respect to a first component, itself integral with a second component which is adjustable in position on a vertical rod of a thoracic support, said end being integral in terms of displacement with a means borne by the first component and capable of being stressed in translation with respect to this first component by a screw or the like.

BRIEF DESCRIPTION OF THE DRAWINGS

Other characteristics and advantages of the invention will become clear from the detailed description which follows and in which reference will be made to the attached drawings, in which.

DETAILED DESCRIPTION OF PREFERRED EMBODIMENTS

Figure 1:
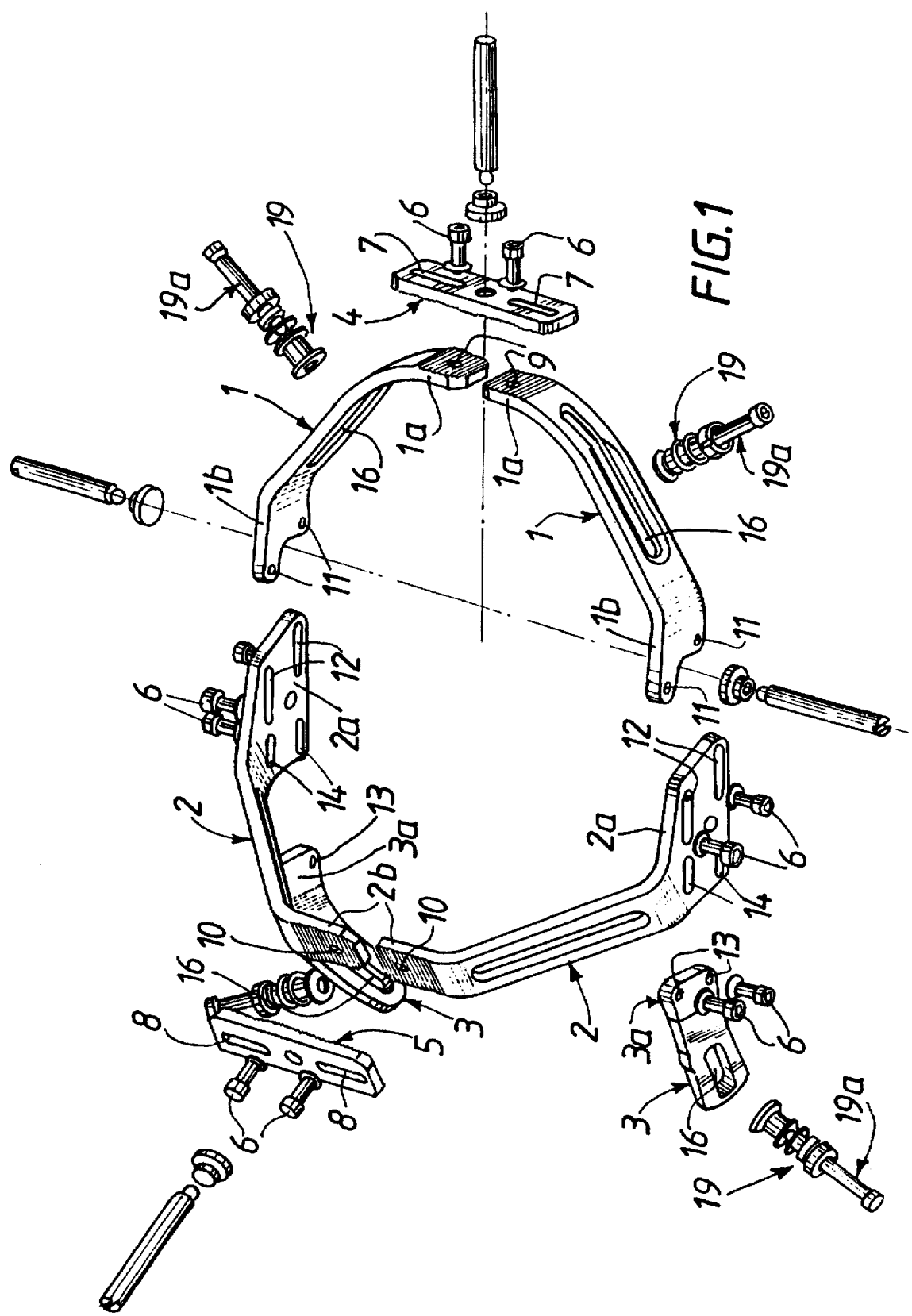
FIG. 1 is an exploded view of a first embodiment of the halo according to the invention.
Figure 2:
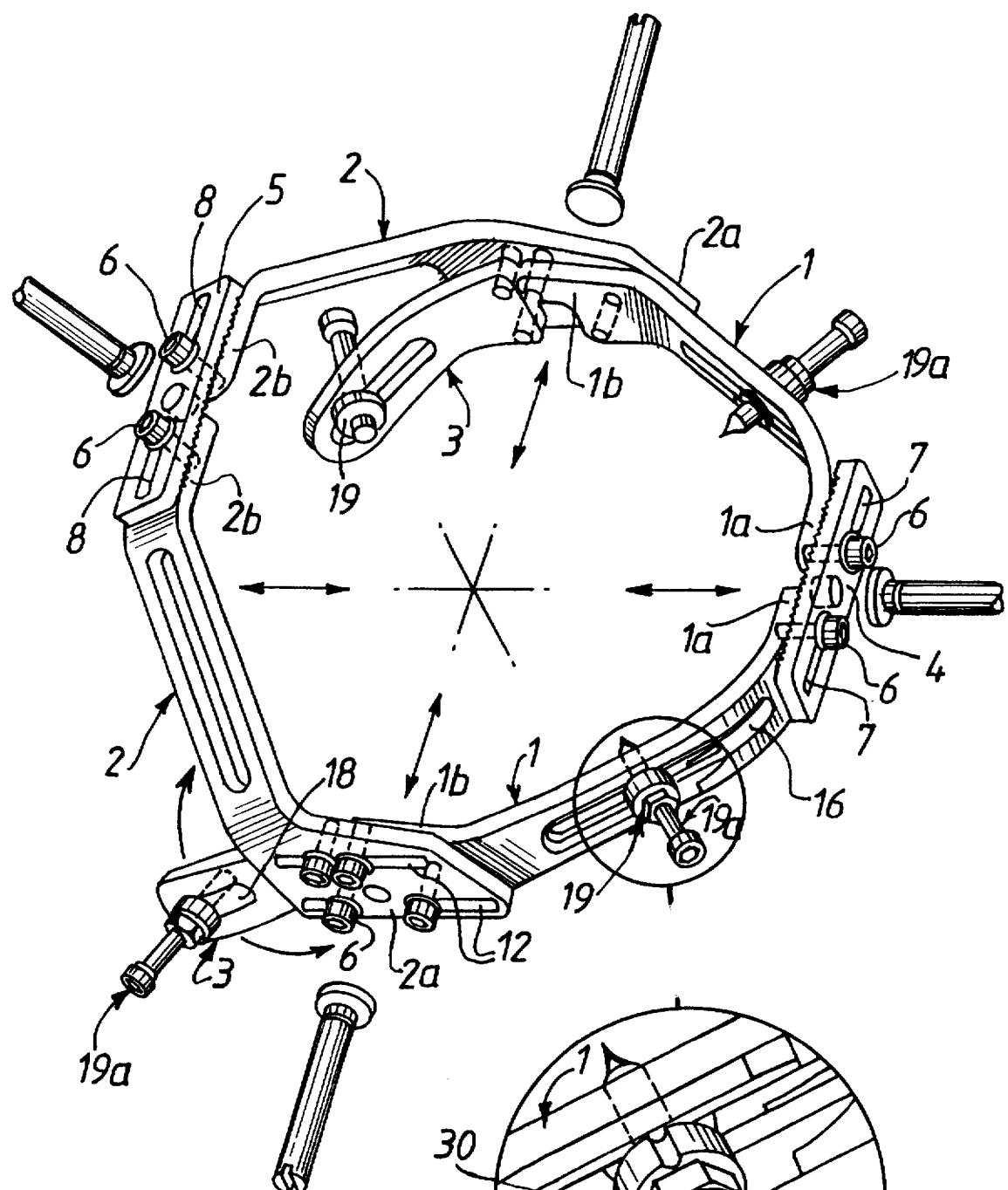
FIG. 2 is a perspective view of the halo in FIG. 1, after the constituent components have been joined together.
Figure 3:
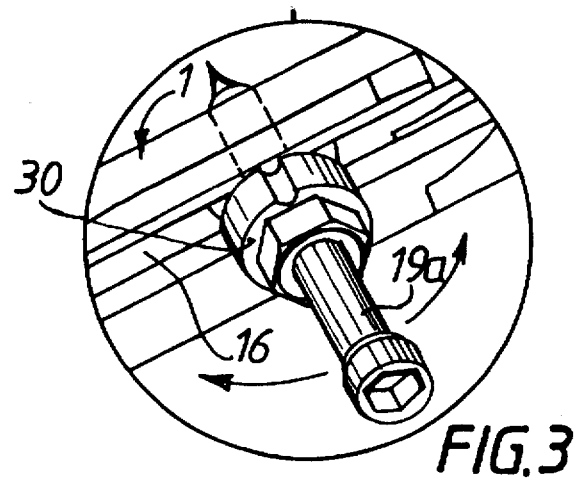
FIG. 3 is a detail view of this halo on a larger scale.

Reference will first be made to FIGS. 1 to 3.

The halo represented in these figures comprises:

two frontotemporal bars 1 intended to bear respectively opposite the left and right frontotemporal zones of the cranium of the patient and opposite the frontal zone, and to be joined to each other;

two half-arches 2 which are intended to be made integral with the frontotemporal bars and to be joined to each other to form one arch which goes over the posterosuperior part of the cranium of the patient;

two occipital bars 3 which are intended to bear, respectively, to the left and to the right in relation to the occipital bones of the patient and to be made integral with a curved end 2a of the half-arches 2 contiguous with the associated frontotemporal bars.

The aim of the invention is to make it possible to adapt the shape and the dimensions of a halo of this type to braincases of different morphologies.

To this end, as can be seen from the drawings, the contiguous frontal ends 1a of the bars 1 and the contiguous posterosuperior ends 2b of the half-arches 2 are joined together with the aid of small bars 4 and 5, respectively, which are applied against these ends, and screws 6 engaged, on the one hand, in oblong slots 7 and 8, respectively, of the small bars 4 and 5, and, on the other hand, in circular orifices 9 and 10, respectively, formed in the ends 1a and 2b facing the oblong slots 7 and 8.

It is thus possible to join together, on the one hand, the frontotemporal bars, and, on the other hand, the half-arches 2 in a plurality of positions by shifting the contiguous ends 1a and 2b, respectively, in order to adapt them to the shape of the braincase of the patient.

In an analogous manner, the end 1b of the frontotemporal bars, opposite the end 1a of these bars, comes to bear against the contiguous end 2a of the half-arches 2 in order to bring orifices 11 of the end 1b into the axes of the two parallel oblong slots 12 formed respectively in the contiguous end 2a of the half-arches 2. It is thus possible to shift the contiguous ends 1b and 2a longitudinally with respect to each other in order to select the assembly position best adapted to the morphology of the cranium of the patient.

Finally, in accordance with the same principle, one end 3a of the occipital bars comes to bear against a face of the contiguous end 2a of the associated half-arch or half-arches 2, in such a way as to bring two orifices 13 of the end 3a into the axis of the two oblong slots 14 of the ends 2a. In this way, it is therefore once again possible here, with the aid of screws 6, to join the occipital bar 3 and the associated half-arch 2 together in a plurality of positions, after translation and/or rotation, in order to adapt to the shape of the braincase of the patient.

It is of course also desirable to be able to adapt to the morphology of the cranium of the patient the position and orientation of the setting screws which are used to fix the halo onto the braincase.

To this end, oblong slots 16 are formed respectively in the frontotemporal bars 1 and in the occipital bars 3, in order to receive the support guides 19 for the setting screws 19a, which are maintained in position by washers and nuts. So that the support guides 19 can be oriented in the most judicious manner, they have a slightly spherical bearing surface, a flattened part on the cylindrical body preventing rotation in the oblong slots, which makes it possible to pivot them by several degrees, as can be seen in FIG. 3, before locking them in position with the aid of nuts 30.

It will be noted that the parts of the small bars 4 and 5 facing the parts 1a of the bars 1 or the parts 2b of the half-arches 2 have corrugated surfaces of complementary profile which prevent any risk of an accidental relative sliding of the surfaces in contact. The corrugated surfaces could be replaced by any other immobilizing means known in the art.

Figure 4:
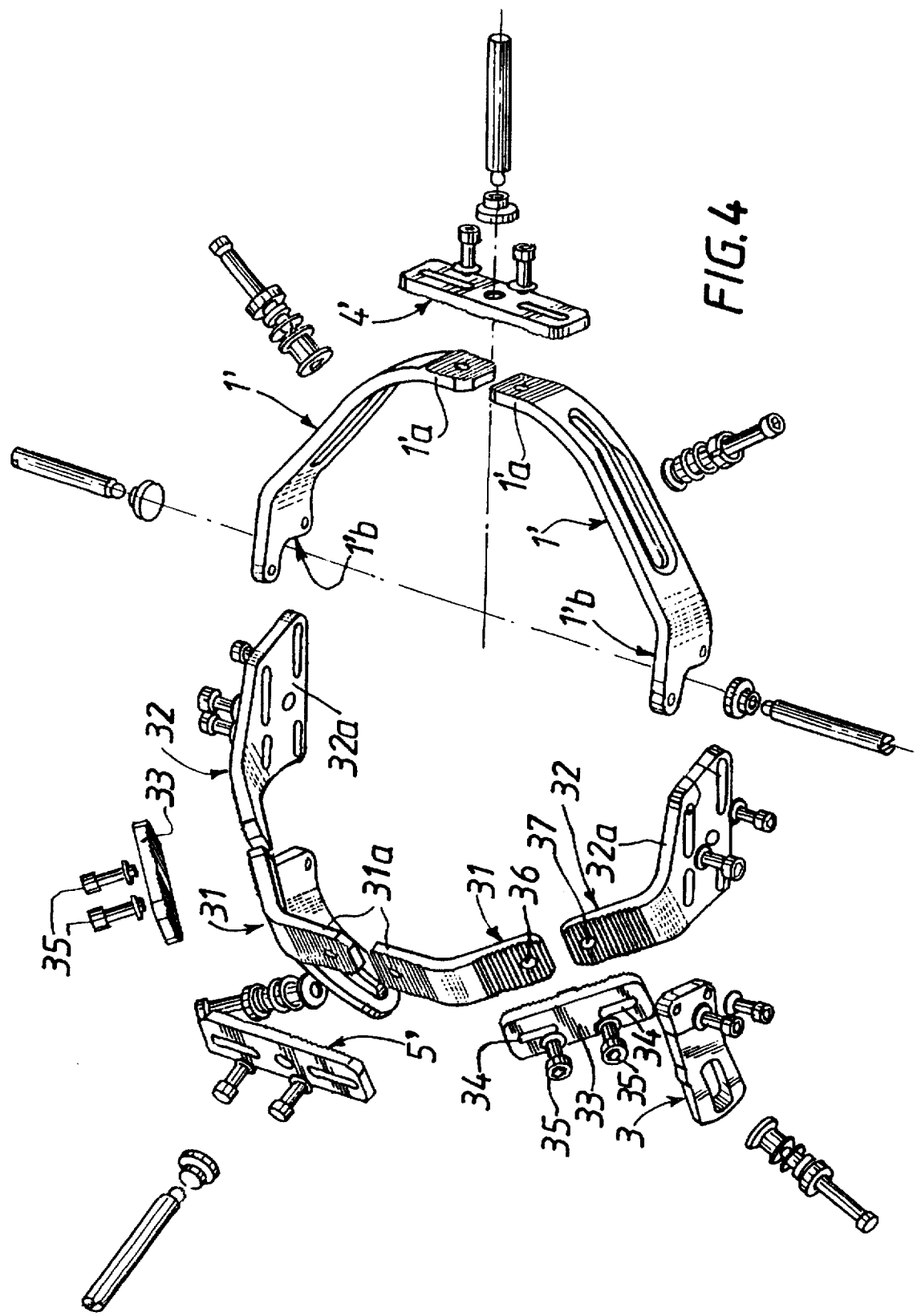
FIG. 4 is a view, similar to FIG. 1, of a second embodiment of the halo according to the invention.

In the alternative in FIG. 4, the same constituent members as in the embodiment in FIG. 1 are for the most part found once again. The members which have already been described are designated by the same reference numbers which are allocated the sign ', and these will not be described over again. The only difference from FIG. 1 is that the half-arches 2 are each replaced by two separate parts which can be joined to each other in a plurality of adjustable positions, namely:

a part 31 to which is adjoined a curved end 31a which cooperates with the small bar 5';

a part 32 to which is adjoined a curved end 32a which cooperates with the end 1'b of the frontotemporal bar 1'.

A small bar 33 pierced by two oblong slots 34 allowing the parts 31 and 32 to be joined together in a plurality of adjustable positions with the aid of screws 35 which are engaged in the desired position in the slots 34 and in orifices 36 and 37 pierced in the parts 31 and 32, respectively.

In this embodiment it is therefore possible to adjust the height of the half-arches formed by joining the parts 31 and 32 together, so as to adapt them to the morphology of the patient.

The halo according to the invention can be made integral with any thoracic support frame used in the art.

Figure 5:
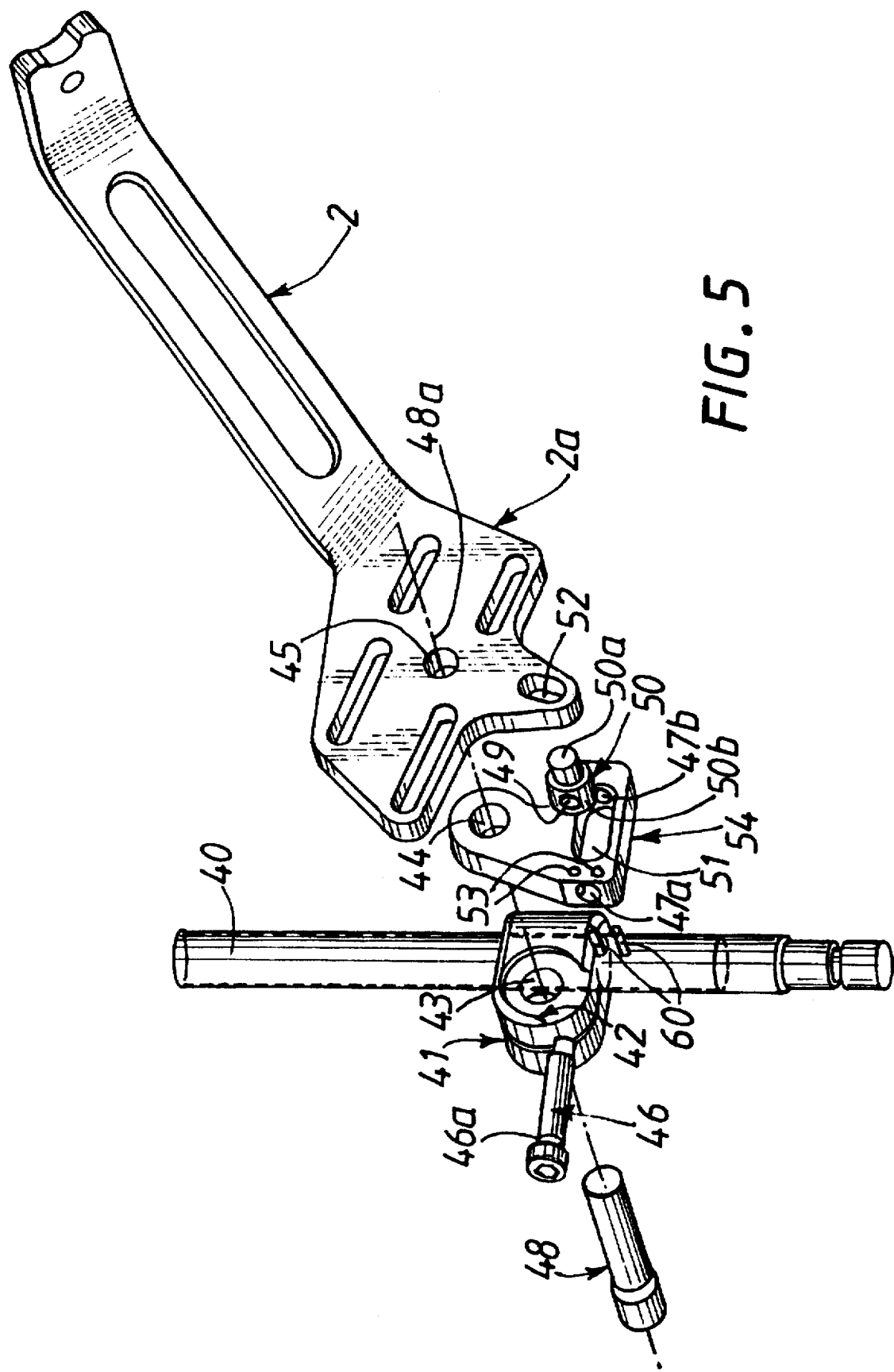
FIG. 5 is an exploded perspective view illustrating a way of fixing the halo in FIGS. 1 to 3 on vertical rods of a thoracic support.

FIG. 5 is an exploded perspective view illustrating a way of fixing the halo in FIG. 1 onto two vertical cylindrical rods 40 of such a thoracic support.

A U-shaped clamp 41 is screwed onto each threaded rod 40 and includes a countersink 42 in which there is accommodated, and immobilized terms of rotation, in a part of complementary shape of an auxiliary component 54, interposed between the clamp 41 and the end 2a of the associated half-arch 2. A screw 48, engaged in orifices 43, 44, 45 of the clamp 41, the component 54 and the end 2a of the half-arch 2, respectively, allows these members to be joined, and its axis 48a serves as a pivot axis for the half-arch 2.

A screw 46 is engaged in smooth guide holes 47a, 47b of the component 54 and is screwed into a threaded hole 49 of a stud 50, one part 50b of which is accommodated in an oblong hole 51 of the component 54, directed along the axis of the screw 46, while a part 50a protrudes laterally from the component 54 and is engaged in an oblong hole 52 of the part 2a, in which hole it can slide. Two pins 60 are engaged in orifices 53 of the component 54, their axis being perpendicular to the axis of the screw 46, and they come to rest in a groove 46a formed in this screw, below the head thereof, in order to immobilize it in terms of translation while allowing it freedom of movement in terms of rotation.

When the screw 46 is driven in rotation, said screw confers a translational movement on the component 50 in the oblong hole 51. The part 50a of the component 50 is displaced simultaneously in the oblong hole 52 of the part 2a, thereby conferring on the half-arch a rotational movement about the axis 48a, which movement, for the halo, and consequently for the cranium/cervical spine unit, translates into a flexion or extension movement, depending on the direction of the rotation.

We claim:

1. A halo which is fixable in a plurality of adjustable positions on the cranium of a patient, said halo comprising at least two frontotemporal bars (1) which are joined to each other and are configured to enclose the forehead and the temples of the patient; two half-arches (2) which are joined to each other and are fixedly connectable with the frontotemporal bars, said joined half-arches forming an arch configured to enclose the posterosuperior zone of the cranium of the patient; bars (4, 5) interconnecting the frontotemporal bars (1) and the half-arches (2) by overlapping contiguous ends thereof, the mutually facing portions of the frontotemporal bars, the half-arches and the interconnecting bars each possessing orifices (7, 8, 9, 10, 11, 12); assembly screw means (6) extending through said orifices to fixedly attach said components to each other, at least some of the orifices of the interconnecting bars (4, 5), of the frontotemporal bars (1), and of the half-arches (2) being oblong slots (7, 8, 12) to facilitate adjustment of the overlap of the interconnecting bars and the ends of the components attached thereto and thereby to adapt the dimensions of the halo to the morphology of the cranium of the patient.

2. A halo according to claim 1, wherein the frontotemporal bars (1) and the half-arches (2) are joined directly to each other, said components including mutually overlapping contiguous end portions (1b, 2a) having said orifices (11, 12) formed therein; said assembly screw means (6) extending through said orifices (11, 12) to fixedly interconnect said components, at least some of the orifices in the adjoining end parts of the frontotemporal bars and the half-arches being said oblong slots (12) so as to facilitate adjusting the overlap of the components and adapt the dimensions of the halo to the cranium of the patient.

3. A halo according to claim 1, wherein the frontotemporal bars (1) and the half-arches (2) are interconnected by joining components partially overlapping the ends of the frontotemporal bars, orifices being formed in mutually facing portions of said joining components and of the frontotemporal bars; and screw means for rigidly fastening together said mutually facing portions, at least some of the orifices of the joining components and of the frontotemporal bars being oblong slots so as to facilitate interconnection thereof in a plurality of adjustable positions.

4. A halo according to claim 2, wherein the half-arches (2) and the frontotemporal bars (1) are connected by said interconnecting bars overlapping contiguous ends of said components, orifices being formed in facing portions of the half-arches and the joining components for receiving fastening screws, at least some of the orifices of said interconnecting bars and of said components being oblong slots so as to facilitate interconnection thereof in a plurality of adjustable positions.

5. A halo according to claim 1, wherein occipital bars (3) are provided to bear against the occiput of the patient, said occipital bars being selectively fastened fastened to ends (2a) of the half-arches (2) and joining components which are contiguous with the frontotemporal bars, through fastening screws (6) engaged in orifices (13, 14) formed in the components which are interconnected, and at least some of said orifices being oblong slots (14).

6. A halo according to claim 5, wherein the frontotemporal bars (1) and the occipital bars (3) include oblong slots (16); and support guides (19) engaged therein for setting screws (19a) which facilitate fixing of the halo on the cranium of the patient.

7. A halo according to claim 6, wherein a bearing surface of each of the support guides (19) for the setting screws (19a) is spherically curved to facilitate orienting the setting screws (19a).

8. A halo according to claim 5, wherein the end (2a) of one of the half-arches (2) and the end (1b) of one said frontotemporal bar (1) are pivotably mounted relative to a first component (54) which is rigidly fastened to a second component (41) adjustably positioned on a rod (40) of a thoracic support, said ends being integrally displaceable with a structure (50) carried by the first component (54) and adapted to be stressed in translation by screw means (46) with respect to said first component (54).

9. A halo according to claim 1, wherein the half-arches comprise two components (31, 32) which are joinable in adjustable positions.

10. A halo according to claim 9, wherein the components (31, 32) of the half-arches are joined through bars (33) having oblong recesses (34) in which screws (35) are engaged in adjustable positions, said screws being engaged in orifices (36, 37) formed in the components (31, 32).

* * * * *

UNITED STATES PATENT AND TRADEMARK OFFICE
CERTIFICATE OF CORRECTION

PATENT NO. : 5,674,186

DATED : October 7, 1997

INVENTOR(S) : Pierre Guigui, et al.

It is certified that error appears in the above-identified patent and that said Letters Patent is hereby corrected as shown below:

On the Title Page, Section [30], line 1: "Sep. 3, 1995" should read --Mar. 9, 1995--

Column 1, line 11: "rerates" should read --relates--

Signed and Sealed this

Fifth Day of January, 1999

Attest:

*Attesting Officer*

*Acting Commissioner of Patents and Trademarks*